(12) United States Patent
Fitzgerald et al.

(10) Patent No.: US 9,463,313 B2
(45) Date of Patent: Oct. 11, 2016

(54) SENSOR-ASSISTED CATHETER-BASED PROCEDURES

(75) Inventors: Peter J. Fitzgerald, Portola Valley, CA (US); Ali Hassan, Mountain View, CA (US); Brian K. Courtney, Toronto (CA)

(73) Assignee: Flea Street Translational, LLC, Menlo Park, CA (US)

( * ) Notice: Subject to any disclaimer, the term of this patent is extended or adjusted under 35 U.S.C. 154(b) by 1818 days.

(21) Appl. No.: 11/720,012

(22) PCT Filed: Nov. 22, 2005

(86) PCT No.: PCT/US2005/042567
§ 371 (c)(1),
(2), (4) Date: Jul. 28, 2009

(87) PCT Pub. No.: WO2006/058132
PCT Pub. Date: Jun. 1, 2006

(65) Prior Publication Data
US 2009/0299445 A1 Dec. 3, 2009

Related U.S. Application Data

(60) Provisional application No. 60/630,917, filed on Nov. 24, 2004.

(51) Int. Cl.
*A61B 5/04* (2006.01)
*A61N 1/05* (2006.01)

(52) U.S. Cl.
CPC .................................... *A61N 1/056* (2013.01)

(58) Field of Classification Search
CPC ................. A61B 18/1492; A61B 2018/0212; A61B 2018/1467; A61B 2018/00214; A61B 5/6852; A61B 5/0084; A61B 17/3421; A61N 1/056; A61N 1/0424; A61N 1/044; A61N 1/0488; A61N 1/0558; A61N 1/0565; A61N 1/0568; A61N 1/057; A61N 1/0573; A61N 1/0575; A61N 1/0587; A61N 1/059
USPC .......... 607/116, 122; 600/373–381; 174/105, 174/110, 113, 114
See application file for complete search history.

(56) References Cited

U.S. PATENT DOCUMENTS

| | | | |
|---|---|---|---|
| 5,330,522 A | 7/1994 | Kreyenhagen | |
| 5,454,809 A * | 10/1995 | Janssen | 606/41 |
| 5,967,984 A * | 10/1999 | Chu et al. | 600/439 |
| 6,127,410 A * | 10/2000 | Duhaylongsod | 514/478 |
| 6,501,991 B1 | 12/2002 | Honeck et al. | |
| 6,510,348 B2 * | 1/2003 | Clemens | A61N 1/056 607/119 |
| 2003/0060868 A1 * | 3/2003 | Janke et al. | 607/123 |
| 2003/0212394 A1 * | 11/2003 | Pearson et al. | 606/41 |
| 2004/0015193 A1 * | 1/2004 | Lamson et al. | 607/9 |

* cited by examiner

*Primary Examiner* — Mallika D Fairchild
(74) *Attorney, Agent, or Firm* — Bret E. Field; Bozicevic, Field & Francis LLP

(57) ABSTRACT

Methods, systems and devices for effectively and safely accessing and verifying a target site within a vessel or body cavity undergoing a catheter-based procedure or treatment. The present invention further includes the accurate delivery an instrument, an implantable device and/or materials to the target site. The present invention is particularly useful for transvenously assessing the suitability of a target site within the coronary vasculature for placement of a pacing electrode and transvenously placing the pacing electrode at the target site.

25 Claims, 3 Drawing Sheets

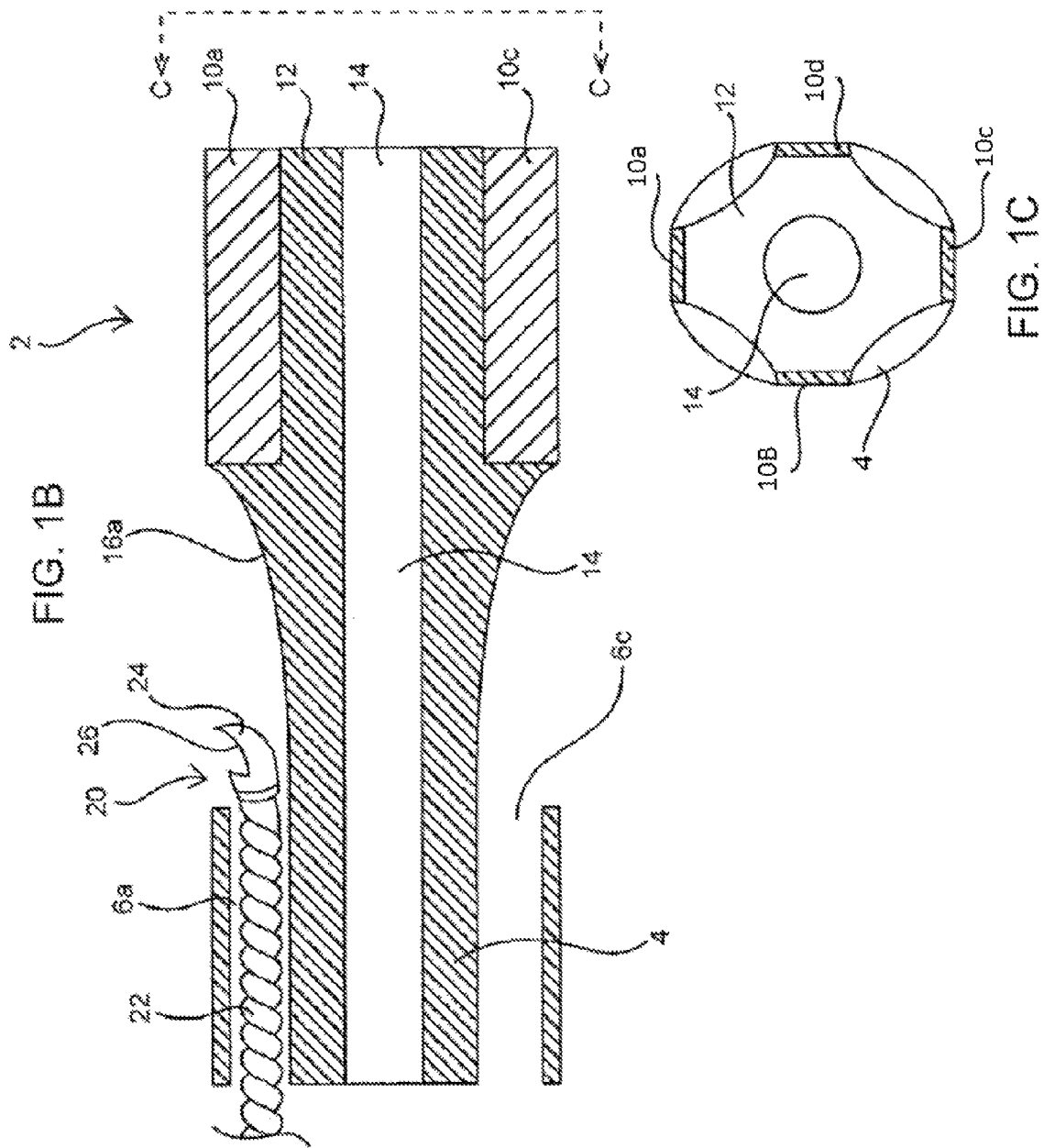

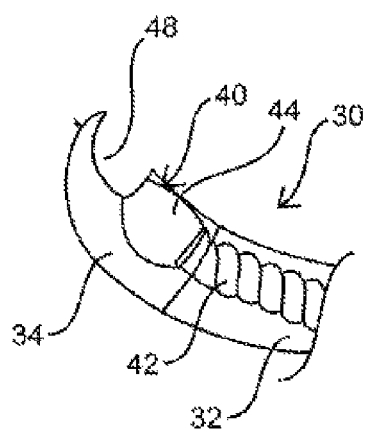
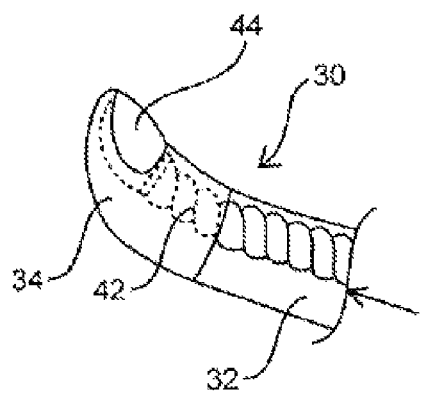
FIG. 2A　　　　　　　FIG. 2B
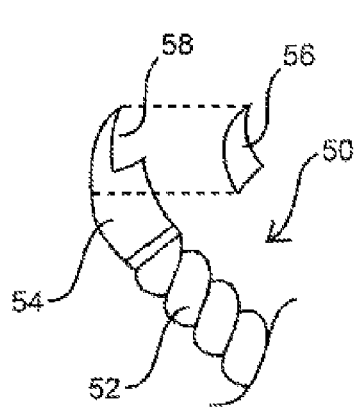
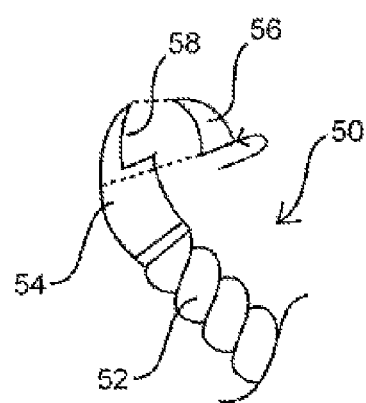
FIG. 3A　　　　　　　FIG. 3B

SENSOR-ASSISTED CATHETER-BASED PROCEDURES

BACKGROUND

Sensors are used in various catheter-based procedures. Imaging sensors or transducers, e.g., intravascular ultrasound (IVUS) transducers, are used to help navigate the delivery of a catheter to a target site or otherwise properly orient the catheter or another instrument or device once at the target site. For example, U.S. Pat. No. 6,685,648 discloses use of an intravascular ultrasound catheter which is delivered to a remote tissue region targeted for treatment. Once at the targeted area, the catheter is properly oriented to position a needle lumen at the region. The needle is then deployed and a drug is injected into the region through the needle lumen. The catheter is configured with a single needle lumen and exit port which requires that the catheter be torqued about its longitudinal axis to rotate its distal end until the needle exit port is aligned relative to the targeted tissue region. Ultrasonic imaging is used, and in fact is required, to observe the orientation of the catheter and to ensure proper alignment of the needle with the target tissue region.

There are certain drawbacks to the catheter systems such as those disclosed in the '648 patent. Due to the unilateral configuration of the catheter, torquing of the catheter is necessary to properly align the "working" portion of the catheter, e.g., the needle exit port, with the targeted tissue region. For a catheter to be adequately torquable, certain material and physical properties are required, e.g., larger gauge, stiffer, etc., which may limit its application in smaller, more tortuous regions of the vasculature. Additionally, the catheters are required to be fitted with an orientation or imaging means such as ultrasonic transducers, which can add to the size and complexity of the system. Ultrasound in particular is limited to imaging of soft tissue, whereby pathologically calcified tissues (such as heart valves in elderly pats) or metallic structures (such as stents, guidewire) present a barrier for ultrasound penetration and imaging of tissue. Furthermore, ultrasound is complex, requires large and expensive image acquisition systems, and complex circuit designs of imaging catheters leading to increased catheter sizes. In addition, ultrasound does not provide ability to sense chemical, or electrical signals of gradients across vessel walls. Specifically, a single ultrasound transducer would produce single-dimension ultrasound signal, usually referred to as M-mode. However, chemical, physical, and biological sensors of comparable size can deliver information regarding location of a target tissue site across a membrane, e.g., a vessel wall. While less complex and size-constrained sensing means, such as chemical, electrical, thermal, biological markers placed near the distal end of a catheter may be used, these sensing methodologies may not be as accurate as ultrasound in many circumstances.

Other types of sensors, i.e., non-imaging sensors, are employed to either measure or sense various parameters in the form of signals (e.g., electrical, biochemical, thermal, biological etc) from within a vessel or body cavity. These sensors maybe configured for either temporary or permanent placement within the body. Such sensors are commonly used for the implantation of pacemakers. Implantable pacemakers are commonly used to treat hearts with abnormal rhythms in such a way that the timing and conduction of the normal cardiac electrical activity necessary for cardiac function is replaced or supplanted by artificially initiated electrical stimuli. A pacemaker consists of a pulse generator and one or more electrodes attached to the pulse generator by means of a lead or insulated wire. The electrodes may be employed to continuously monitor electrical activity of the heart as well as to transmit electrical pulses from the pulse generator to the cardiac tissue in response to the sensed signals. The output pulses cause depolarization and contraction of cardiac tissue to help in restoring cardiac function.

Pacemakers are commonly implanted in a minor surgical procedure during which the patient is mildly sedated and given a local anesthetic. Through an incision near the clavicle, the pulse generator is implanted under the skin and the leads are inserted into a vein leading to the heart. The leads are then advanced transvenously to the heart using continuous fluoroscopic guidance. The electrode is then positioned or fixed to a target site within a coronary vein within the heart, or on the surface of the heart inside the pericardial cavity.

Transvenous pacing of the left ventricle presents significant difficulties. As effective pacing requires that the electrodes be accurately placed at targeted pacing sites within the coronary veins, a catheter having imaging or sensing means is required for placing the electrodes. Due to the tortuous path to the cardiac veins, including the coronary sinus, and the small size of the distal cardiac veins, the drawbacks of current imaging catheter technologies discussed above also apply here.

Epicardially-placed electrodes can be used to pace the left ventricle. In contrast to a transvenous lead, an epicardial lead is attached to the outside of the heart. Placement of an epicardial lead requires that the surface of the heart be exposed, for example by a thoracatomy, and involves considerable operative risk in these already very sick patients. Thus, while epicardial pacing of the left ventricle is available, transvenous pacing is often more desirable.

With the limitations of current catheter technologies, there is clearly a need for an improved means and method of accessing and verifying a target site within a vessel lumen or a body cavity undergoing a catheter-based procedure, particularly a site targeted for the implantation of a device (e.g., pacing electrode, etc.) or the delivery of a material (e.g., drugs, saline, biologic compositions, etc.).

SUMMARY OF THE INVENTION

The present invention provides methods, systems and devices for effectively and safely accessing and verifying a target site from within a vessel, tissue lumen or body cavity (where the target site may be inside or outside of the vessel) undergoing a catheter-based procedure or treatment. The present invention further includes the accurate delivery of an instrument, an implantable device and/or materials to the target site. The present invention is particularly useful for transvenous identification of a target site located in a vessel periphery for placement of a pacing electrode and transvenously placing the pacing electrode at the target site.

The systems include a catheter having at least one sensing element at a distal end and at least one delivery lumen terminating at a distal port. The sensing element is used to sense and measure various parameters in the form of signals (e.g., electrical, biochemical, thermal, biological etc) from within a vessel or body cavity. The sensed signals may be representative of hemodynamic function and response. The sensed signal may be capable of being sensed across the vessel wall. From these measurements, a target site can be determined and assessed. For example, a preferred pacing or electrode placement location can be determined. The delivery lumen extends substantially axially within or along the catheter body and terminates at a port or opening at the distal end of the catheter. The port or opening is associated with, e.g., relatively aligned with, the sensing element whereby an instrument, e.g., a tissue perforating tool, may be optimally delivered and employed, and/or a device, e.g., pacing electrode, may be optimally placed.

Certain variations of the systems include catheters having multiple sensing elements and corresponding coaxial delivery lumens and associated exit ports. As such, the systems may provide complete or circumferential sensing. Such circumferential sensing eliminates or reduces the need to rotate the catheter.

The subject systems may further include a guidewire to facilitate delivery of the catheter to a target site. The guidewire is deliverable through a lumen of the catheter (and may be associated with a sensing element delivering a desired signal) and the catheter is translatable or tractable over the guidewire. The subject guidewires may be further configured to function as tissue penetrating, cutting or puncturing implements. Additionally or alternatively, the guidewires may serve as pacing leads which may be implanted at a target site and left within or outside the vasculature upon removal of the catheter.

The methods include use of the subject catheter systems to perform a medical procedure. The medical procedure may include one or more of sensing electrical and/or hemodynamic signals, accessing a target site within or outside the vasculature, penetrating a tissue structure such as a vessel wall, body cavity or mural site, anchoring an electrode at a target site and implanting a pacing lead at the target site.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1B illustrates a side cross-sectional view of the catheter system of FIG. 1A.

FIG. 1C illustrates an end view of the catheter system of FIG. 1B taken along lines C-C.

FIGS. 2A and 2B illustrate an embodiment of a guidewire for use with the systems of the present invention.

FIGS. 3A and 3B illustrate another embodiment of a guidewire for use with the systems of the present invention.

DETAILED DESCRIPTION OF THE INVENTION

Figure 1A:
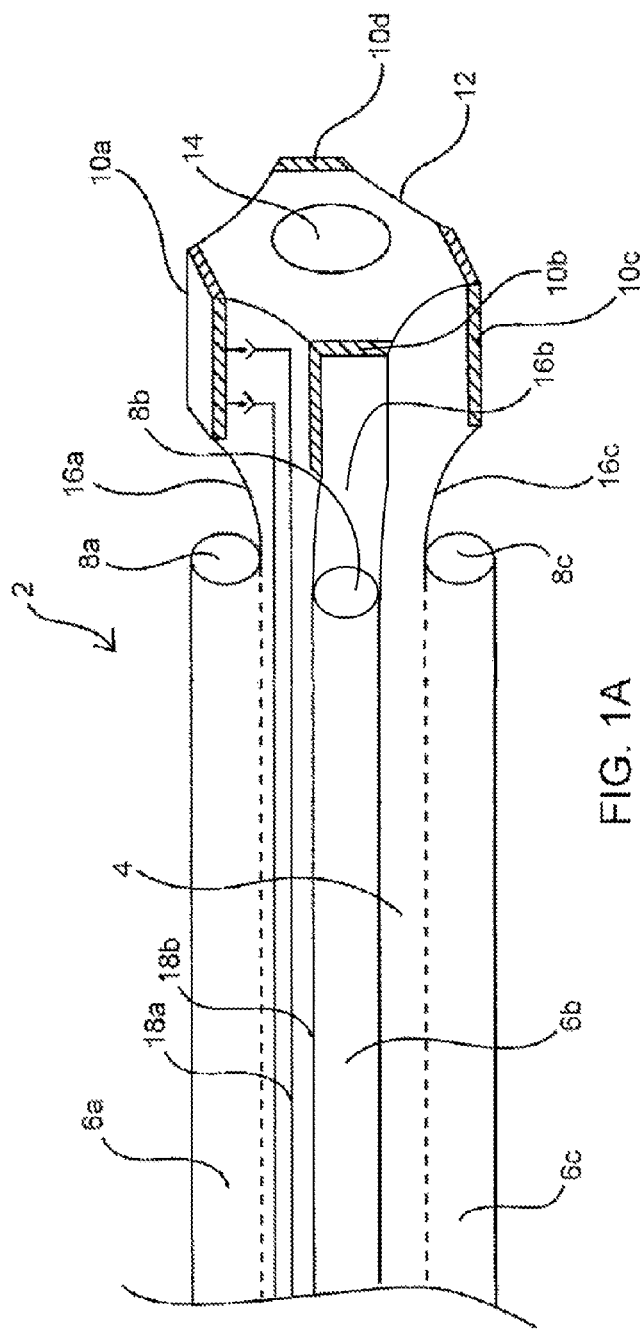
FIG. 1A illustrates a perspective view of an embodiment of a catheter system of the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a sensor" includes a plurality of such sensors and reference to "the catheter" includes reference to one or more catheters and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Referring now to the representative embodiments of various aspects of the invention as depicted in the Figures, a distal end of a catheter system 2 of the present invention is illustrated in FIGS. 1A-D. System 2 includes a catheter body 4 having a distal end portion 12 having a plurality of elements 10a-d spaced-apart about the circumference or external surface of the distal end of catheter 4. The elements may be sensors or transducers for assessing or determining the location of the distal end of the catheter based on information sensed or measured about the catheter's environment. Alternatively, the elements may be imaging markers for establishing the axial location or rotational orientation of the catheter's distal end. Still yet, elements 10 may include a combination of sensors and imaging elements, e.g., a sensor may be positioned between two imaging markers and vice-versa, or each element may have a sensing portion and an imaging portion.

Where the elements are sensors or transducers, each element 10 is coupled via signal-carrying leads 18a, 18b to an external energy measurement device (not shown) for detecting and measuring energy emanating from tissue contacted by or adjacent to the sensor. The configuration of the energy measurement device and associated sensors will vary according to the selected energy modality, e.g., electrical, thermal, electrochemical, biochemical, biological, radioactive, acoustic, optical, static, etc., employed. A variety of different physiological parameters may be sensed, including but not limited to: electrical pulses, changes in pH values, changes in $pO_2$ or $pCO_2$, changes in EKG patterns, changes in wall distensibility patterns, changes in cross-sectional blood flow, e.g., side branch, etc. The sensors employed may vary, and will be chosen based on the nature of the physiological parameter of interest. For example, where electrical pulses are to be sensed, the sensors are electrodes. For analyte detection, e.g., the sensors are electrodes coated with a reagent material selected for reacting with the targeted analyte. For temperature detection, the sensors are temperature sensors, e.g., thermocouplers or thermistors. Where elements 10 are imaging markers, the markers are made of a radiopaque or fluoroscopic material (coupling leads 18a, 18b are not necessary).

The orientation elements 10 are preferably planar and flush with the outer surface of catheter body 4, and may have any suitable shape. Thus, while elements 10 are shown having a rectangular shape, they may be circular, square, oblong, etc. Additionally, while four elements 10 are shown evenly spaced from each other, the subject systems are not limited to such a configuration. Any suitable number of elements 10, from one to five or more, may be employed with any suitable spacing relationship, i.e., symmetrical or asymmetrical. For example, a single annular or semi-annular element may extend continuously or partially about the periphery of catheter distal end 12. The particular number and arrangement of positioning elements 10 may depend on the type of element used and the application at hand. For example, where the orientation elements are sensors, a preferable orientation element arrangement, regardless of the number of sensors used, is one which provides sufficient circumferential (360°) sensing without having to torque or axial rotate catheter body 4.

Extending parallel along the longitudinal axis of catheter body 4 is a plurality of channels, conduits or lumens 6a-d. As with elements 10, any number of channels 6 may be employed with the subject systems. In certain embodiments, there is a one-to-one correspondence between the number of channels 6 and the number of elements 10. Channels 6a-d terminate distally at corresponding side ports or openings 8a-d, respectively, positioned peripherally about the catheter's distal end. A ramped surface 16a-d may be provided at each port 8a-d to outwardly direct an instrument or the like delivered through the port 8. Each corresponding exit port 8 is axially aligned with and proximal to a corresponding element 10. However, the ports 8 may be axially offset from elements 10, for example, where each exit port is axially aligned between two adjacent elements. Additionally, the catheter may be configured where elements 10a-d are positioned proximally of exit ports 8a-d. While ports 8a-d are shown having a profile which is transverse to the longitudinal axis of catheter 4, they may alternatively be flush with and located within the outer surface or periphery of the catheter. Still yet, one or more or all of the ports may be provided on the forward-facing distal surface of the catheter. For example, an optional central lumen 14 may be provided within catheter body 4 which lumen 14 extends distally of the other lumens and terminates in an opening at the distal tip of the catheter body.

The various lumens 6 and 14 are used for delivering or transporting instrumentation for performing a surgical and/or devices (e.g., a smaller catheter, guidewire, energy-applicator, cutting instrument, tissue removal instrument, pacing leads, etc.) to be implanted at a target site. Alternatively or additionally, the lumens may be used to deliver materials such as fluids, e.g., drugs, saline (such as for inflating a balloon), biologic compositions (e.g., for gene therapy), or the like, as well as to remove, i.e., aspirate, materials harvested or embolized at the target site. The delivery lumens may all be used to deliver the same type of instrument or material or each may be particularly configured to deliver a particular type of device or material, e.g., one lumen may be used as a guidewire lumen, another may be used as a blood bypass channel, another may be used to deliver a cutting instrument, another may be used to deliver a pacing lead, etc. Where more than one lumen is provided, one of the lumens, either the central or a peripheral lumen, may be used exclusively as a guidewire lumen while the others are used as delivery, inflation, bypass and/or aspiration lumens.

Figure 1D:
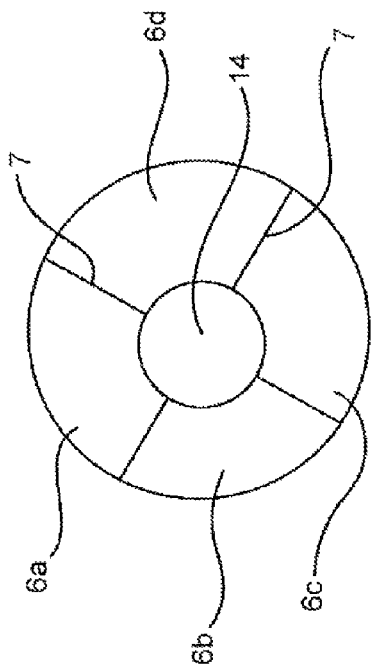
FIG. 1D illustrates a cross-sectional view of an embodiment of a catheter system of the present invention.

In one embodiment, as illustrated in the cross-sectional view of catheter body 4 in FIG. 1D, lumens 6 may be configured so that they are separated from each other (and lumen 14) by thin, compliant walls 7. This configuration is advantageous for at least a couple of reasons. First, the compliant walls 7 can accommodate instruments of varying diameters. Additionally, the walls bordering an unoccupied lumen may be expanded into the unoccupied lumen to accommodate instruments occupied in adjacent lumens which instruments have cross-sectional dimensions which are larger than diameter of the lumens in their natural, unexpanded state.

In one embodiment, one or more lumens 6 may be used to deliver a tissue-penetrating device 20 (shown in FIG. 1B) for the purpose of puncturing, coring, piercing or incising tissue adjacent the external wall of catheter 4. Tissue-penetrating device 20 includes an elongated body 22 and a distal tip 24 configured to perform the intended tissue-penetrating function. Body 22 may be made of any suitable material such as materials commonly used to fabricate guidewires. In certain embodiments, body 22 may have a wire form made of shaped-memory material, e.g., NITINOL, where the material is predominantly stiff and has a preformed distal bend or curve. The distal tip of the guidewire is designed to assume two different configurations: a first traumatic configuration, which enables the guidewire to pierce through a vascular wall thereby facilitating access to target tissue; and a second configuration that is "non-traumatic" or atraumatic, which configuration enables guidewire to serve as a navigational instrument, once introduced into target tissue or cavity. As such, when the distal portion is made to exit from a lumen 6a through a port 8a, it is allowed to transform to the preformed configuration and extend radially outward toward the contacted tissue. Ramped surface 16a further facilitates the outward trajectory of the distal end portion.

Upon deployment from port 8, distal tip 24 is transformed into its traumatic configuration, and is caused to penetrate the contacted tissue, such as a wall of a blood vessel to access a target tissue site or tissue region beyond the vessel wall, i.e., outside of the vessel. Distal tip 24 may have any suitable shape and configuration for penetrating tissue in a desired manner. For example, in the illustrated embodiment, distal tip 24 has a hook or claw configuration where the pointed tip can be used to penetrate tissue. Distal tip 24 further includes a cutout region 26 on its concave surface. The edges of cutout region 26 may be sharp or blade-like to cut into tissue. So as to prevent inadvertent damage to tissue, distal tip 24 may be retained within lumen 6a until the catheter is optimally positioned at a target site. Once at the target site, device 20 may be advanced a sufficient axial distance to allow deployment of distal tip 24 from exit port 8a.

In one variation, device 20 may function as a guidewire as well as a tissue-penetrating instrument. To this end, distal tip 24 may have a blunt or non-traumatic configuration when device 20 is used as a guidewire, and may be converted to a hook, claw or other suitable configuration for penetrating tissue. With the non-traumatic configuration, device 20 functions as a guidewire and can be used in the same manner as a conventional guidewire. Specifically, guidewire 20 can be advanced to a target site within the body and catheter 4 may then be delivered or translated over the guidewire (through any lumen 6 or 14) to the target site. Once at the target site, distal tip 24 is converted to a tissue-penetrating configuration and employed as such.

FIGS. 2A and 2B illustrate one embodiment of such a dual-function device. Device 30 includes an elongated body 32 having a hollow distal working tip 34 having a traumatic configuration as described above. Elongated body 32 may be hollow or otherwise provide a lumen which can accommodate an inner core member 40 having an elongated body 42 and a bulbous or rounded distal tip 44 which are axially translatable within body 32. Tip 44 is sized and shaped to sealingly engage against cutout 48 of distal work tip 34 such that a flush, smooth, non-traumatic surface is provided about tip 34 when core member 40 is advanced distally within hollow body 32. Hollow body 32 may also be used to deliver other instruments, devices or materials to a target site when not occupied by core member 40.

FIGS. 3A and 3B illustrate another embodiment of a dual function device. Device 50 includes an elongated body 52, which may be solid or hollow, having a distal working tip 54 having a traumatic configuration as described above. Tip 54 includes a shutter or cover 56 which is sized and configured to close cutout 58 within tip 54. Shutter 56 may be either internally or externally engaged with tip 54 and may be either rotationally or linearly translatable to open and close the opening 58. When shutter 56 is in the closed position, tip 54 has a flush, smooth, non-traumatic surface.

The systems of the present invention may be configured and sized, and have material or physical characteristics suitable for any application and function. For example, catheters of the present invention used for cardiovascular applications will have dimensions and material characteristics similar to conventional cardiovascular catheters. Likewise, catheters of the present invention used for alimentary applications will have dimensions and material characteristics similar to conventional alimentary catheters. With any configuration, preferably the diameter of catheter body 4 about the lumens 6 is constant along its length, i.e., is the same about lumens 6 as about elements 10, so as to provide a smooth, non-traumatic surface, particularly through narrow passageways. Further, the systems may employ mechanisms and functions of conventional catheter systems, including for example, steering mechanisms, visualization markers, etc.

Use of the subject systems is now described in the context of cardiac pacing lead implantation in which a subject system is percutaneously and transvenously delivered to a target site within one or more coronary veins, however, such application is intended to be exemplary and not limiting as the present invention may be used in a variety of applications, including but not limited to endocardial (i.e., within a heart chamber) and epicardial (i.e., on the outer surface of the heart) cardiac pacing lead implantation, gastrointestinal tract pacing lead implantation, etc., as well as a variety of other applications not involving the placement of pacing leads, e.g., applications involving the urinary bladder, various regions of the central nervous system, the pancreas, etc.

An embodiment of the subject system configured for cardiac pacing lead implantation includes a catheter as generally described above. The catheter's sensors function as temporary or permanent electrodes to provide means for electrical stimulation to the contact cardiac tissue and subsequently sensing the electrical response thereto. As such, the best locations for subsequent transvenous pacing, i.e., the best locations for permanently placing the pacing electrodes, can be determined. Here, the multi-lumen approach provides circumferential sensing without the requirement of rotating the catheter during operation. In certain embodiments, a single sensor provides a desired signal, and the corresponding lumen is used to introduce the penetrating device and pacing leads. In such embodiments, other lumens associated with other sensors may remain idle. On the other hand, where the number of electrodes to be placed is greater than the number of delivery lumens, the electrodes may be delivered in sequential sets where the catheter can be "reloaded" with subsequent sets of pacing electrodes. Still yet, in order to reduce the size of the catheter a single, larger electrode transport lumen may be provided which branches distally into a plurality of exit ports. The pacing electrodes may be individually loaded or bundled together and simultaneously loaded, with each respective distal tip then directed to a single exit channel.

In certain embodiments, the pacing electrodes are placed evenly spaced from each other, as such, the luminal openings are evenly spaced about the circumference of the catheter. As a sensor can substantially identify a precise optimal location for the placement of a pacing electrode, it is also preferable to provide a one-to-one correspondence between the number of sensors and the number of lumens and their associated exit ports where each port is axially aligned with a corresponding sensor. In certain embodiments, one provides complete circumferential (i.e., 360°) sensing of the tissue surrounding the catheter without having to rotate or torque the catheter. Accordingly, at least about four sensors are used where each sensor has the ability to sense signals within at least a 90° angle range. Fewer or more sensors may be used depending on the sensing range of each sensor.

In a representative embodiment for use in electrode placement applications, the above-described tissue-penetrating instruments also function as the pacing electrodes. The distal tips define electrodes and the connected elongated bodies define wire leads which are proximally attachable to an implanted pacemaker. Either prior to or subsequent to delivery of the catheter to a target site within the coronary venous system, the pacing electrodes are loaded into the delivery lumens and distally advanced towards their respective exit ports. Depending on the stiffness of the pacing leads, one of the electrodes may be employed as a guidewire as described above. Alternately, a separate designated guidewire may be provided through a central lumen of the catheter.

One or more of the orientation elements or sensors may be made of or coated with a radiopaque material to act as a marker for imaging by an external imaging system used to provide guidance in delivery the catheter to within the coronary venous system. Additional markers may also be provided along the length of the catheter to facilitate delivery. Upon reaching a possible appropriate stimulation location, such as in the coronary sinus or further distally into a coronary vein, the sensors are activated for assessment of various electrical and hemodynamic parameters, e.g., electrocardiogram sensing of PH differences, sensing of distensibilities of various segments of vessel wall, sensing of differences in cross-sectional blood flow, etc. for obtaining appropriate transvenous pacing. If such appropriate criteria are not obtained, the catheter is linearly translated to another potentially suitable location within the coronary venous system. Once a proper position for transvenous pacing or stimulation has been found, the pacing electrodes are deployed from their respective lumens and their distal tips are caused to penetrate the vessel wall to a suitable depth which will provide permanent anchoring of the pacing leads. In order to ensure accurate sensing and deployment of the pacing electrodes, it may be necessary to minimize movement of the catheter caused by the natural motion of the heart and by the intravenous blood pressures. To this end, a stabilizing or anchoring mechanism, such as an expandable or inflatable member may be provided on the catheter at a position either proximal or distal to the sensors and electrode deployment ports. Expansion or inflation of the member, e.g., a balloon, may be controlled by one of the catheter lumens, e.g., providing delivery of saline to inflate the balloon.

It is known that electrical conductance within the myocardium can most easily be effected or interfered with by electrical stimulation originating closest to the epicardial surface. Accordingly, it is preferable to embed the pacing electrodes within the portion of the vessel wall closest to the epicardial surface. As such, deployment of the pacing electrodes may be selective such that, for example, only the pacing electrodes within the lumens that substantially face, oppose or are adjacent to the epicardial surface are deployed. The epicardial side of the heart may be determined by sensing and/or by imaging. This may involve deployment of about 50% or fewer of the available pacing electrodes. With catheter embodiments providing evenly spaced lumens about the entire circumference of the catheter where each is loaded with a pacing electrode, as opposed to just having one or more electrode deployment lumens located on only one side or portion of the catheter, no rotational translation or torquing of the catheter is necessary in order to properly position the pacing electrodes towards the epicardial surface.

Upon deployment of the pacing electrodes, the lumens from which electrodes have been deployed may be reloaded with additional pacing electrodes and the above steps repeated. To most efficiently perform the electrode implantation procedure and avoid unintentional dislodgement of the implanted electrodes by subsequent translation of the catheter, it is preferable to implant electrodes at the most distally anticipated location within the venous system. This avoids having to track the catheter over previously implanted electrodes. As such, the catheter should be advanced to the most distal anticipated implantation site where sensing is preformed and a first set of electrodes is implanted. The catheter can then be retracted proximally to the next anticipated implantation site where sensing is again performed a second set of electrodes may be implanted. The procedure is repeated as necessary wherein the catheter is progressively translated proximally through the vasculature; however, subsequent distal translations of the catheter may be performed as necessary to enter into additional vessels into which pacing leads may need to be implanted. Upon completion of the electrode lead placements, the catheter is withdrawn from the body and the electrodes are left temporarily or permanently implanted within the vasculature. The necessary coupling of the proximal end of the pacing leads may then be made to a pacemaker.

Depending on the number of electrode deployment lumens, the lumens may have to be reloaded for subsequently placed electrode sets. Where a significant number of lumens is provided, for example from about 5 to about 20 or more, e.g., ranging in sized from about 0.5 French to about 6 French in certain embodiments, reloading may not be necessary; however, some rotational translation of the catheter may be necessary to accurately place subsequent sets of pacing electrodes. It should also be noted that the greater the number of electrode deployment lumens, the larger the catheter diameter, which may limit the size of the vessels into which the catheter may be employed.

Delivery of the catheter, deployment of the pacing electrodes and retraction of the catheter, as well as other steps of the subject methods, if necessary, may be performed with or without videoscopic or endoscopic assistance or intra-operative transesophageal echocardiogram (TEE).

The subject devices and systems may be provided in the form of a kit which may include one or more of the above described catheters and/or a plurality of the above described pacing electrodes. The kits may further include catheter-based instruments deliverable through the catheters for performing a medical procedure. Additionally, the kits may include implantable devices, such as sutures, clips, etc., which are also deliverable through the catheters. Instructions for using the various devices and systems may also be provided with the kits.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A catheter system comprising:
   a catheter body having a length extending between a proximal and a distal end;
   a plurality of sensors positioned on an outer surface of said catheter body at said distal end; and
   a plurality of lumens extending along said length, wherein there is a one-to-one relationship between said sensors and said lumens and each of said lumens terminates in an opening onto an outer surface of said catheter body, wherein said opening:
   (a) is axially aligned and proximally positioned with a sensor of said plurality of sensors; and
   (b) is separated from said sensor of said plurality of sensors by a ramp on an outer surface of said catheter body that is positioned between said sensor and said opening, wherein said ramp is curved such that an elongated member emerging from said opening is outwardly deflected by said ramp away from said catheter body.

2. The catheter system of claim 1, wherein said openings are positioned about a periphery of said distal end.

3. The catheter system of claim 1, wherein said sensors are electrical sensors.

4. The catheter system of claim 1, wherein said sensors are biochemical sensors.

5. The catheter system of claim 1, wherein said sensors are acoustic sensors.

6. The catheter system of claim 1, further comprising at least one additional lumen extending axially along said catheter length and terminating at an opening at said distal end.

7. The catheter system of claim 6, wherein said additional lumen is positioned centrally with respect to said plurality of lumens.

8. The catheter system of claim 7, wherein said central lumen is a guidewire lumen.

9. The catheter system of claim 7, wherein said central lumen is a fluid bypass lumen.

10. The catheter system of claim 1, wherein at least one of said lumens is a guidewire lumen.

11. The catheter system of claim 1, further comprising at least one elongated member configured for delivery through at least one of said lumens.

12. The catheter system of claim 11, wherein said at least one elongated member comprises a distal tip configured to penetrate tissue.

13. The catheter system of claim 12, wherein said distal tip comprises a traumatic configuration and a non-traumatic configuration.

14. The catheter system of claim 12, wherein said distal tip comprises a pacing electrode.

15. The catheter system of claim 14, wherein said pacing electrode is a cardiac pacing electrode.

16. The catheter system of claim 1, further comprising a plurality of pacing electrodes configured for delivery through said plurality of lumens.

17. The catheter system of claim 1, wherein adjacent lumens are separated from each other by compliant walls.

18. A kit comprising:
a catheter system according to claim 1; and
instructions for performing a catheter-based procedure using said catheter and said plurality of elongated members.

19. The kit of claim 18, wherein said catheter-based procedure is a pacing lead implantation procedure and said elongated members comprises pacing electrodes.

20. The catheter system of claim 1, wherein an inflatable anchoring unit is positioned proximate to the sensors and configured to control a positioning of the catheter body at a target site.

21. The catheter system of claim 1, wherein the outer surface of the catheter body further includes a plurality of orientation elements configured to control a positioning of the catheter body at a target site.

22. The catheter system of claim 1, wherein the system comprises four pairs of sensors and lumens.

23. A catheter system comprising:
a catheter body having a length extending between a proximal and a distal end;
a plurality of sensors positioned on an outer surface of said catheter body at said distal end;
a lumen extending along said length; and
a plurality of openings in communication with said lumen and each opening onto an outer surface of said catheter body, wherein each of said openings:
(a) is axially aligned with and proximally positioned to a sensor of said plurality of sensors; and
(b) is separated from said sensor of said plurality of sensors by a ramp on an outer surface of said catheter body that is positioned between said opening and said sensor, wherein said ramp is curved such that an elongated member emerging from said opening is outwardly deflected by said ramp away from said catheter body.

24. The catheter system of claim 23, further comprising a plurality of elongated members configured to be individually translated through said lumen.

25. The catheter system of claim 23, further comprising a plurality of elongated members configured to be collectively translated through said lumen, wherein each said opening is configured to deploy a single elongated member.

* * * * *